United States Patent
Ogata et al.

(10) Patent No.: US 8,420,129 B2
(45) Date of Patent: Apr. 16, 2013

(54) CHLORINE DIOXIDE SOLUTION COMPOSITION

(75) Inventors: Norio Ogata, Osaka (JP); Takashi Shibata, Suita (JP); Kazuhiko Taguchi, Sakai (JP); Koichi Doi, Otsu (JP)

(73) Assignee: Taiko Pharmaceutical Co., Ltd., Osaka (JP)

( * ) Notice: Subject to any disclaimer, the term of this patent is extended or adjusted under 35 U.S.C. 154(b) by 172 days.

(21) Appl. No.: 12/812,705

(22) PCT Filed: Jan. 19, 2009

(86) PCT No.: PCT/JP2009/050658
§ 371 (c)(1),
(2), (4) Date: Oct. 5, 2010

(87) PCT Pub. No.: WO2009/093540
PCT Pub. Date: Jul. 30, 2009

(65) Prior Publication Data
US 2011/0020473 A1  Jan. 27, 2011

(30) Foreign Application Priority Data
Jan. 23, 2008  (JP) ................... 2008-012820

(51) Int. Cl.
*A01N 59/08* (2006.01)
*A61K 33/14* (2006.01)

(52) U.S. Cl.
USPC ........................................................ 424/661

(58) Field of Classification Search ........................ None
See application file for complete search history.

(56) References Cited

U.S. PATENT DOCUMENTS

| 5,326,546 | A | * | 7/1994 | Rosenblatt et al. | ........... 423/241 |
| 6,284,152 | B1 | * | 9/2001 | Kross | ........... 252/187.21 |
| 2004/0231977 | A1 | | 11/2004 | Roselle et al. | |
| 2006/0068029 | A1 | | 3/2006 | Mason | |

FOREIGN PATENT DOCUMENTS

| JP | 61-181532 A | 8/1986 |
| JP | 7-315806 A | 12/1995 |
| JP | 11-130407 A | 5/1999 |
| JP | 3110724 B2 | 11/2000 |
| JP | 2003-55120 A | 2/2003 |
| JP | 2006-526076 A | 11/2006 |
| JP | 2007-537969 A | 12/2007 |
| WO | WO 2006/068743 | 6/2006 |

OTHER PUBLICATIONS

International Search Report (PCT/ISA/210) issued on Feb. 24, 2009, by Japanese Patent Office as the International Searching Authority for International Application No. PCT/JP2009/050658.
Takanori Miura et al., Molecular Mechanism of *Feline calicivirus* Inactivation by Novel Chlorine Dioxide Solution, Journal of Pharmaceutical Society of Japan, Oct. 1, 2006, vol. 126, Suppl. 3, pp. 100-101.
International Preliminary Report on Patentability (Form PCT /IB/ 373) and Written Opinion of the International Searching Authority(Form PCT/ISA/237) mailed in International Application No. PCT/JP2009/050658, Sep. 10, 2010, The International Bureau of WIPO, Geneva, CH.

* cited by examiner

*Primary Examiner* — James H. Alstrum-Acevedo
*Assistant Examiner* — Daniel L Branson
(74) *Attorney, Agent, or Firm* — Buchanan Ingersoll & Rooney PC

(57) ABSTRACT

There are provided a chlorine dioxide solution composition whose solute includes dissolved chlorine dioxide and chlorite; and a solution composition encapsulating body including a glass vessel or enameled vessel and the chlorine dioxide solution composition hermetically sealed therein.

10 Claims, 1 Drawing Sheet

Glass bottle: $C = 19\exp(-0.05t) + 82$
Synthetic resin (PET) bottle: $C = 87\exp(-0.02t) + 13$

CHLORINE DIOXIDE SOLUTION COMPOSITION

TECHNICAL FIELD

The present invention relates to a chlorine dioxide solution composition (hereinbelow, also simply referred to as "solution composition"), a solution composition encapsulating body, a method for preserving a chlorine dioxide solution composition, and a method for maintaining the concentration of dissolved chlorine dioxide in a chlorine dioxide solution composition. In particular, the present invention relates to: a chlorine dioxide solution composition containing substantially no pH adjuster consisted of acid, such as citric acid, that has been believed to be an essential component; an above-described chlorine dioxide solution composition encapsulating body including a glass vessel or enameled vessel and the chlorine dioxide solution composition hermetically sealed therein; a method for preserving an above-described chlorine dioxide solution composition including a process of hermetically sealing the chlorine dioxide solution composition in a glass vessel or enameled vessel; a method for maintaining the concentration of dissolved chlorine dioxide including a process of hermetically sealing the chlorine dioxide solution composition in a glass vessel or enameled vessel; and a chlorine dioxide solution composition for treatment of fungal disease, viral disease and bacterial disease.

BACKGROUND ART

It is well known that chlorine dioxide gas is a strong oxidant, and its oxidizing action is effective in sterilization and decomposition of malodorous substances. Therefore, chlorine dioxide has been used in disinfectant, deodorant and the like. Chlorine dioxide is dissolved in water in 20 times its volume of water, to give a yellowish brown aqueous solution. From the viewpoint of handling, it is desirable to use chlorine dioxide in a form of such an aqueous solution. However, when the aqueous solution of chlorine dioxide is brought into contact with air, chlorine dioxide gas is rapidly generated. Therefore, there has been proposed a technique in which stability of chlorine dioxide gas is maintained by dissolving chlorine dioxide gas in an aqueous solution of sodium peroxycarbonate ($Na_2C_2O_6$), and thus by forming an aqueous solution containing sodium chlorite ($NaClO_2$) as a main component at a retained pH of 9, i.e., what is called a stabilized aqueous solution of chlorine dioxide (see Patent Document 1).

The stabilized aqueous solution of chlorine dioxide is, however, retained at pH 9 (alkali) for the purpose of maintaining stability, as described above. Accordingly, the generation amount of free chlorine dioxide gas having disinfecting and deodorizing effects or the like is extremely low, and thus it is difficult to attain satisfactory disinfecting and deodorizing effects or the like.

Therefore, it has been proposed that, immediately before its use, a stimulant is added to the stabilized aqueous solution of chlorine dioxide, or an acid is added to lower the pH to 7 or less, for generating chlorine dioxide gas. However, with this technique, there arise economical problems that equipments or facilities to implement such processes are required.

In addition, the retention of the generation of chlorine dioxide from the stabilized aqueous solution of chlorine dioxide depends solely on the concentration of the contained chlorine dioxide, and therefore there is a problem which should be fundamentally remedied in that the development of a product having the retention of the generation of chlorine dioxide suitable for intended use is extremely difficult.

In order to solve the above-mentioned problems, there has been proposed a technique in which a mixture prepared by adding a pH adjuster formed of an organic acid, such as citric acid, to chlorite is blended with a solution of chlorine dioxide dissolved therein, to thereby obtain a three-component mixture which can maintain a chlorine dioxide concentration nearly constant for a long term (see Patent Documents 1 and 2). With this technique, the preservation stability of chlorine dioxide can be remarkably enhanced, and the chlorine dioxide concentration can be maintained constant for a long term.

Patent Document 1: Japanese Unexamined Patent Application Publication No. 61-181532

Patent Document 2: Japanese Patent Publication No. 3110724

DISCLOSURE OF THE INVENTION

Purpose of the Invention

With respect to the long-term preservation technique of the solution of chlorine dioxide dissolved therein, the present inventors made intensive and extensive studies with the view toward discovering further effective technique. As a result, they discovered that by hermetically sealing in a glass vessel or enameled vessel a solution composition composed of two components (dissolved chlorine dioxide and chlorite), excluding the pH adjuster that has been believed to be an essential component, the dissolved chlorine dioxide concentration can be maintained nearly constant for a long term, and completed the present invention.

In one aspect of the chlorine dioxide solution composition of the present invention, a solute thereof includes dissolved chlorine dioxide and chlorite.

In another aspect of the chlorine dioxide solution composition of the present invention, a solute thereof is composed of two components including dissolved chlorine dioxide and chlorite.

In still another aspect of the chlorine dioxide solution composition of the present invention, the solute thereof includes dissolved chlorine dioxide and chlorite, and the composition contains substantially no pH adjuster.

It is preferable that the chlorine dioxide solution composition is used for treatment of fungal disease, viral disease and bacterial disease. In addition, it is preferable that a concentration of the dissolved chlorine dioxide is 0.1-500 ppm, that the chlorite is salt of alkali metal chlorite or salt of alkali earth metal chlorite, that the salt of alkali metal chlorite is sodium chlorite or potassium chlorite, and that a concentration of the chlorite is 500-50,000 ppm.

In one aspect of the solution composition encapsulating body of the present invention, it includes a glass vessel or enameled vessel and any of the above-described chlorine dioxide solution composition hermetically sealed therein.

In one aspect of the method for preserving the chlorine dioxide solution composition of the present invention, it includes a process of hermetically sealing any of the above-described chlorine dioxide solution composition in a glass vessel or enameled vessel.

In one aspect of the method for maintaining the concentration of dissolved chlorine dioxide in a chlorine dioxide solution composition of the present invention, it includes a process of hermetically sealing any of the above-described chlorine dioxide solution composition in a glass vessel or enameled vessel.

EFFECT OF THE INVENTION

The chlorine dioxide solution composition of the present invention includes only chlorine dioxide and a chlorite as solute, and even though it does not contain the pH adjuster that has been believed to be an essential component, the dissolved chlorine dioxide concentration in the chlorine dioxide solution composition can be maintained nearly constant for a long term. Since excellent preservation stability is obtained without adding the pH adjuster, the chlorine dioxide solution composition is conveniently used in clinical application (especially in application to human body).

BEST MODE FOR CARRYING OUT THE INVENTION

Figure 1:
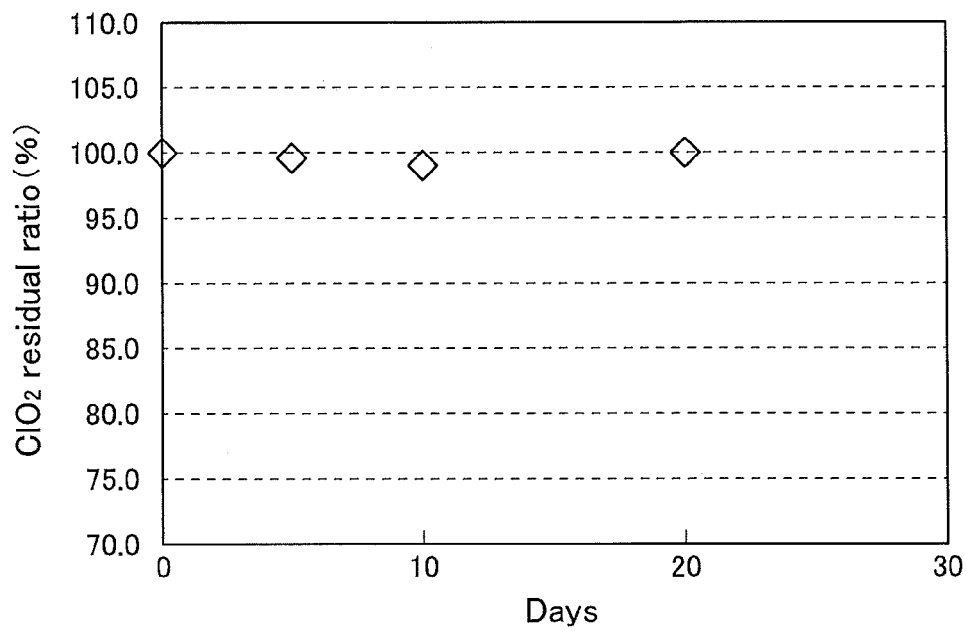
FIG. 1 is a graph showing a change over time of the dissolved chlorine dioxide concentration of the solution composition sealed in a brown (light-blocking) ampule made of glass.

Hereinbelow, one embodiment of the present invention will be described, but it should not be construed that the present invention is limited by these embodiments. In the chlorine dioxide solution composition of the present invention, the solute is composed of dissolved chlorine dioxide and chlorite. Substantially no pH adjuster is contained. The chlorine dioxide solution composition is hermetically sealed in a glass vessel or enameled vessel.

(Preparative Example of Chlorine Dioxide Solution)

The chlorine dioxide solution may be, for example, manufactured in the following manner.

Specifically, chlorine dioxide gas is bubbled and dissolved in water to prepare 100-2,900 ppm of dissolved chlorine dioxide (aqueous solution of chlorine dioxide) (a). Also, chlorite is dissolved in water to prepare 2,000-180,000 ppm of an aqueous chlorite solution (b). Subsequently, 5.0-990 ml, preferably 50-800 ml of the aqueous solution of chlorine dioxide dissolved therein (a) and 5.0-990 ml, preferably 50-800 ml of the aqueous chlorite solution (b) are mixed and stirred well at room temperature, to thereby prepare a chlorine dioxide solution composition of the present invention.

(Chlorite)

As chlorite, for example, salts of alkali metal chlorite and salts of alkali earth metal chlorite can be mentioned. Examples of the salt of alkali metal chlorite include sodium chlorite, potassium chlorite and lithium chlorite. Examples of the salt of alkali earth metal chlorite include calcium chlorite, magnesium chlorite and barium chlorite. Especially, not only from the viewpoint of availability, but also from the viewpoint of excellent sustention of generation of chlorine dioxide gas, sodium chlorite and potassium chlorite are preferable, and sodium chlorite is more preferable.

(Preservation Container (Glass Vessel, Enameled Vessel))

As container for preserving the solution composition, any container can be used, as long as the container has a body whose most portions (90% or more, preferably 95% or more of the surface area) is made of glass, and a substance to be filled (the solution composition) can be reliably hermetically sealed therein. Examples include ampule, vial, screw cap vial, and hermetically sealed preservation bottle made of glass.

The container body may be transparent or brown with a light-blocking property, but a brown light-blocking glass is preferable from the viewpoint of excellent preservation stability of the solution composition. The solution composition may be filled and sealed using a well-known commercially available ampule filler/sealer machine (ampule sealer) or vial filler/capper machine, and if desired, nitrogen or argon substitution may be performed.

Even in the case of the container which is frequently opened for the use of the solution contained therein, it is desirable that the sealability of the plug part is robust and the container has a structure which suppresses the dissipation of the chlorine dioxide gas into the atmosphere when the plug is closed and the container is not used.

In addition, it is preferable to use an enameled container having a glass layer on a body, obtained by glazing and firing the body, such as metal, ceramic, and glass to convert the glaze to have vitreous nature. Specifically, there can be mentioned a container obtained by applying a vitreous glaze containing silica (silicon dioxide) as a main component to a surface of a metal material, such as iron and aluminum, or a ceramic material, and firing the container at a high temperature.

(Other Requirements)

It should be noted that in the solution composition of the present invention, the pH adjuster is intentionally excluded, and contains substantially no pH adjuster. Examples of the pH adjuster herein include organic acid or salt thereof, and inorganic acid or salt thereof. Examples of the organic acids and salts thereof include formic acid, acetic acid, propionic acid, butyric acid, lactic acid, pyruvic acid, citric acid, malic acid, tartaric acid, gluconic acid, glycolic acid, fumaric acid, malonic acid, maleic acid, oxalic acid, succinic acid, acrylic acid, crotonic acid, oxalic acid, glutaric acid, and salts thereof. Examples of the inorganic acids include phosphoric acid, boric acid, metaphosphoric acid, pyrophosphoric acid, and sulfamic acid. Examples of the salts of the inorganic acid include sodium dihydrogenphosphate, and a mixture of sodium dihydrogenphosphate with sodium monohydrogenphosphate.

(Applications)

The chlorine dioxide solution composition of the present invention can be added to, for example, potable water, food processing water, swimming pool water or the like, to thereby perform a disinfection and deodorizing treatment thereon. Specifically, vegetables, table wares, kitchen linens or the like can be disinfected by immersing them into an aqueous solution prepared by diluting the above-prepared chlorine dioxide solution approximately ten-fold with water. Moreover, kitchen facilities at hotels, restaurants, catering industry, schools and household, rooms of house, lavatory pans, car interiors or the like can be disinfected and deodorized, by spraying a dilution onto them prepared by diluting the solution approximately five-fold.

The followings are other applications of the chlorine dioxide solution composition of the present invention, by way of examples.

(1) Nonwoven fabric or woven fabric impregnated with the chlorine dioxide solution composition may be sealed in a package made of synthetic resin or metal foil. This may be used as a wet wipe (disposable hand towel) that is portable and opened when desired, or provided at restaurants to customers.

(2) The composition can be clinically applied to treatment for infections, utilizing antiviral effect, antibacterial effect and antifungal effect of the chlorine dioxide. For example, in the case of the treatment of skin disease and mucocutaneous disease, a gauze, cotton or nonwoven fabric may be impregnated with the solution composition of the present invention containing 0.1-500 ppm, preferably 10-250 ppm of chlorine dioxide, 500-50,000 ppm, preferably 700-20,000 ppm of sodium chlorite, and brought into contact with or inserted into the affected area, for at least five minutes, preferably ten minutes or longer, and this treatment may be repeated once to three times a day. In the case of the ocular or nasal drop, the solution composition of the present invention containing 0.1-500 ppm, preferably 10-250 ppm of chlorine dioxide may be used, and this treatment may be repeated once to six times a day.

(3) The chlorine dioxide solution composition of the present invention may be aerially-sprayed in a room using a known device, to prevent viral disease (caused by, for example, influenza virus), bacterial disease and fungal disease, which will be described below.

(4) A mask or eye patch may be directly impregnated with the chlorine dioxide solution composition, or alternatively, a gauze or nonwoven fabric impregnated with the chlorine dioxide solution composition may be attached to a mask or eye patch, to prevent viral disease, bacterial disease and fungal disease, which will be described below.

(Examples of Viral Disease to be Treated)

As pathogen of viral disease, a wide range of viruses can be mentioned, and examples include influenza virus (types A, B and C), avian influenza virus, norovirus (feline calicivirus), human papillomavirus (HPV: pathogen of cervicitis, malignant adenoma of uterine cervix, and condyloma acuminatum), coxsackievirus (pathogen of hand-foot-and-mouth disease, aseptic meningitis, summer cold, febrile disorder, paralysis and respiratory tract disease), AIDS virus (HIV), hepatitis B virus, canine parvovirus, rotavirus, HHV-1 (herpes simplex virus type 1 (HSV-1)), HHV-2 (herpes simplex virus type 2 (HSV-2)), HHV-3 (varicella-zoster virus (VZV)), HHV-5 (cytomegalovirus (CMV)), virus associated with an ophthalmic field (adenovirus for pharyngoconjunctival fever (water pool fever) and epidemic keratoconjunctivitis (pinkeye); and enterovirus for acute hemorrhagic conjunctivitis).

(Examples of Bacterial Disease to be Treated)

Examples of the bacteria that cause bacterial disease include *Staphylococcus aureus, Pseudomonas aeruginosa, Streptococcus, Neisseria gonorrhoeae* and *Treponema pallidum*, and the composition of the present invention can be used for treating the diseases caused by these bacteria, such as those listed below. Examples include dermatosis, such as acne vulgaris (acne), impetigo contagiosa, decubitus (bedsore), hordeolum (chalazion), blepharitis marginalis, periodental disease (such as alveolar pyorrhea), cellulitis, folliculitis, and staphylococcal scalded-skin syndrome. The present invention may be used for prevention of secondary infection, such as infection of injury, burn and surgical wound.

(Examples of Fungal Disease to be Treated)

Examples of the fungi that cause fungal disease include *Trichophyton, Malassezia* and *Candida*, and the composition of the present invention can be used for treating the diseases caused by these fungi, such as dermatosis listed below. Examples include tinea pedis, tinea corporis, tinea cruris, tinea unguium, other *Trichophyton* infections, candidiasis (such as cutaneous candidiasis and vulval candidiasis), interdigital erosion, erythema mycoticum infantile, paronychia, tinea versicolor, and seborrheic dermatitis.

<Application Region>

Examples of the body regions to which the solution composition of the present invention can be applied include scalp, face, eye (e.g., eyelid, conjunctiva or cornea), ear (e.g., external ear and external canal), nose (e.g., nostril and nasal mucosa), lip, oral cavity, pharynx, larynx, glottis, respiratory mucosa, esophagus, stomach, duodenum, small intestine, colon, tongue, gingiva (gum), neck, portion of torso, limbs (including interdigital area), penis, genital prepuce, vulva, vagina, uterine cervix, endometrium, anus, rectum, and nail. The composition of the present invention is also suitably applied to mucous membrane. In addition, it can be used for skin or skin mucosa, not only of human body, but also of pets, such as the dog and the cat, and domestic animals (such as the cow, the pig, the chicken and the sheep).

Example 1

In the following manner, the chlorine dioxide solution composition was prepared.

Specifically, chlorine dioxide gas was generated using 9% HCl and 25% sodium chlorite, passed through purified water to dissolve therein, by which a 1,200 ppm aqueous solution of chlorine dioxide dissolved therein was prepared.

There were mixed 750 g of the 1,200 ppm aqueous solution of chlorine dioxide dissolved therein and 20 g of a 25% aqueous solution of sodium chlorite to which purified water was added to 5 liter as a total amount, to thereby prepare a chlorine dioxide solution composition having a chlorine dioxide concentration of 150 ppm and a sodium chlorite concentration of 1,000 ppm.

Twenty ml of the prepared chlorine dioxide solution composition was encapsulated in a commercially available brown (light-blocking) ampule made of glass (20 ml volume) and the ampule was hermetically sealed using an ampule filler/sealer machine (ampule sealer) in accordance with a well-known method, to thereby obtain a solution composition encapsulating body (n=4). A stress testing was performed by leaving the ampule (sample) at 60° C. for 20 days, and a residual ratio of chlorine dioxide (%) was measured on day 5, day 10 and day 20, by an ultraviolet-visible spectrophotometer. The results are shown in Table 1 and FIG. 1.

TABLE 1

|  | Day 0 | Day 5 | Day 10 | Day 20 |
| --- | --- | --- | --- | --- |
| ClO$_2$ residual ratio (%) | 100 | 99.5 | 99.1 | 99.8 |

As shown in Table 1 and FIG. 1, the dissolved chlorine dioxide concentration of the solution composition sealed in a brown (light-blocking) ampule made of glass was maintained at 99.8%, even after the stress testing at 60° C. for 20 days.

Example 2

The chlorine dioxide solution composition prepared in Example 1 was placed in a brown (light-blocking) hermetically sealed bottle made of glass as well as in a brown (light-blocking) hermetically sealed bottle made of synthetic resin (PET). The hermetically sealed bottle made of glass and the hermetically sealed bottle made of synthetic resin (PET) are the same in the volume and in the thickness of the container body wall, and the same amount of the chlorine dioxide solution composition was added to each container and the containers were hermetically sealed, to obtain the solution composition encapsulating bodies. With respect to each of the hermetically sealed containers, a change over time of a dissolved chlorine dioxide concentration of the sealed solution composition (in the solution composition encapsulating body) was measured by an ultraviolet-visible spectrophotometer. The results are shown in FIG. 2.

Figure 2:
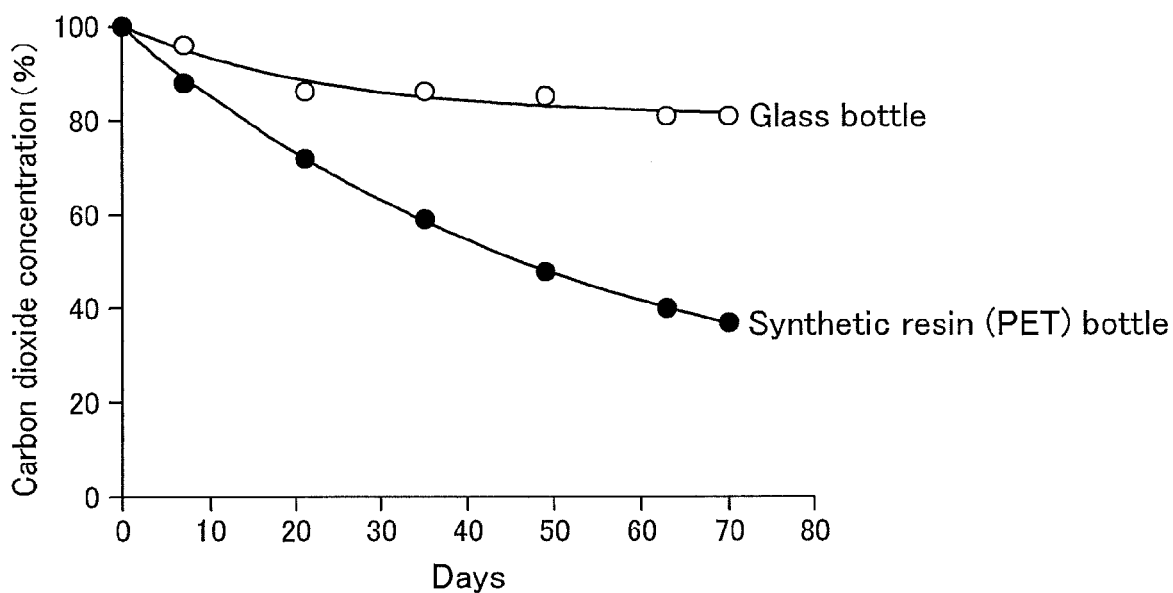
FIG. 2 is a graph showing changes over time of the dissolved chlorine dioxide concentration of the solution composition in a hermetically sealed bottle made of glass and in a hermetically sealed bottle made of synthetic resin (PET), and approximate equations for respective curves.

As shown in FIG. 2, the dissolved chlorine dioxide concentration of the solution composition sealed in the hermetically sealed bottle made of synthetic resin (PET) gradually decreased after the hermetic sealing, to approximately 50% after 50 days, and to less than 40% after 70 days. On the other hand, the dissolved chlorine dioxide concentration of the solution composition sealed in the hermetically sealed bottle made of glass gradually decreased after the hermetic sealing, but the decreasing rate was extremely small as compared with the case of the hermetically sealed bottle made of synthetic resin (PET), and the chlorine dioxide concentration was maintained at 80% or more even after 50 days (concentration reduction: less than 20%). Surprisingly, when encapsulated in the hermetically sealed bottle (ampule) made of glass, the chlorine dioxide concentration became equilibrated at 83%, and no more concentration change (concentration reduction) occurred, and thus the chlorine dioxide concentration was retained at 83% (see FIG. 2).

Example 3

Twenty ml of the chlorine dioxide solution composition prepared in Example 1 was encapsulated in a commercially available brown (light-blocking) hermetically sealed bottle made of glass, and the bottle was hermetically sealed using an ampule filler/sealer machine (ampule sealer) in accordance with a well-known method, to thereby obtain a solution composition encapsulating body. This ampule was left in a cold place for three months, and used for a clinical trial under the cooperation between patients and physicians. Immediately prior to use, the ampule was opened to take out the chlorine dioxide solution composition, and a gauze having a size of 20 cm×20 cm which had been rolled up to a cylindrical shape was impregnated with the chlorine dioxide solution composition and used for trial (after the impregnation of the chlorine dioxide solution composition, the gauze was not squeezed). Descriptions will be made in detail below.

(Clinical Trial 1) <Age 52, Female> (Mycotic Vaginitis)

A 52-year old female came to the hospital two days after a development of a symptom of itch in a vulva and increase in vaginal discharge. Pretreatment finding was that the vulva became congestive, and massive secretion (vaginal discharge) was attached to both labium majus and labium minus. In addition, vaginal mucous membrane was congestive, and massive secretion (vaginal discharge) was observed. The attending physician diagnosed mycotic vaginitis (candidal vaginitis), and for treatment, the above-described rolled gauze (impregnated with the chlorine dioxide solution composition) was inserted into the vagina, and removed 15 minutes later. The patient was instructed to repeat the same treatment every day.

As a result, itch in the vulva disappeared on day three, hyperemia of the vulva began to disappear on day 14, and the hyperemia of the vulva and vagina mucous membrane completely disappeared and the massive secretion disappeared on day 21.

(Clinical Trial 2) <Age 45, Female> (Human Papilloma Virus)

A 45-year old female (with low back pain) who came to the hospital was examined. As a result, it was found that an amount of vaginal discharge was large, uterine cervical erosion swelled (uterine cervical erosion, second degree), and hyperemia and wound were present. The attending physician diagnosed chronic cervicitis, and for treatment, the above-described rolled gauze (impregnated with the chlorine dioxide solution composition) was inserted into the vagina, and removed 15 minutes later. The patient was instructed to repeat the same treatment every day.

As a result, a mouth of the uterus was fused on day seven, and it was confirmed that the symptoms become relatively mild. Human papilloma virus (HPV) level on day 7 was measured in accordance with a well-known method, and the level was 256.28 pg/mL. The same treatment was continued, and on day 14 after the commencement of the treatment, the vaginal discharge was remarkably reduced, and the low back pain was ameliorated. Subsequently, on day 21, the vaginal discharge and the low back pain were further ameliorated, and it was confirmed that the hyperemia and the erosion of the uterine cervix was also ameliorated. The HPV level was reduced to 183.56 pg/mL on day 21.

(Clinical Trial 3) <Age 22, Female> (Human Papilloma Virus)

A 22-year old female who had suffered a large amount vaginal discharge for a long time due to pus came to the hospital and was examined. As a result, the attending physician diagnosed uterine cervical erosion and HPV (human papilloma virus) infection. For treatment, the above-described rolled gauze (impregnated with the chlorine dioxide solution composition) was inserted into the vagina, and removed 15 minutes later. The patient was instructed to repeat the same treatment every day.

As a result, on day seven, the HPV level became 357.21 pg/mL and was remarkably reduced from the pretreatment level of 1176.42 pg/mL. In addition, the vaginal discharge was remarkably reduced.

(Clinical Trial 4) <Age 49, Female> (Bacterial Vaginosis; Bv)

A 49-year old female who came to the hospital with a complaint of a large amount of vaginal discharge was examined. As a result, it was found that the vaginal discharge was purulent, and a large number of bacteria were present in the vaginal discharge. Hyperemia (inflammation) was also found in the vulval and vaginal mucous membrane, and the attending physician diagnosed bacterial vaginosis (BV). For treatment, the above-described rolled gauze (impregnated with the chlorine dioxide solution composition) was inserted into the vagina, and removed 15 minutes later. The patient was instructed to repeat the same treatment every day.

As a result, on day seven, hyperemia (inflammation) of the vulval and vaginal mucous membrane disappeared, and the vaginal discharge was reduced.

INDUSTRIAL APPLICABILITY

The chlorine dioxide solution composition of the present invention can be used for a disinfection and deodorizing treatment on potable water, food processing water, swimming pool water or the like, by adding the solution thereto; a disinfection treatment on vegetables, table wares, kitchen linens or the like by immersing them into the solution; and a disinfection and deodorizing treatment on kitchen facilities at restaurants, catering industry, schools and household, rooms of house, lavatory pans, car interiors or the like, by spraying a solution onto them. The composition can be also used for treating fungal disease, viral disease and bacterial disease.

The invention claimed is:

1. A solution composition encapsulating body comprising a glass vessel or enameled vessel and a chlorine dioxide solution composition whose solute consists of dissolved chlorine dioxide and chlorite, wherein the chlorine dioxide solution composition is hermetically sealed in the glass vessel or enameled vessel.

2. A method for preserving a chlorine dioxide solution composition comprising:
    a step of hermetically sealing the chlorine dioxide solution composition whose solute consists of dissolved chlorine dioxide and chlorite in a glass vessel or enameled vessel.

3. A method for maintaining a concentration of dissolved chlorine dioxide in a chlorine dioxide solution composition comprising:
   a step of hermetically sealing the chlorine dioxide solution composition whose solute consists of dissolved chlorine dioxide and chlorite in a glass vessel or enameled vessel.

4. The solution composition encapsulating body according to claim 1, wherein a concentration of the dissolved chlorine dioxide is 0.1-500 ppm.

5. The solution composition encapsulating body according to claim 1, wherein the chlorite is a salt of alkaline metal chlorite or a salt of alkaline earth metal chlorite.

6. The solution composition encapsulating body according to claim 5, wherein the salt of alkaline metal chlorite is sodium chlorite or potassium chlorite.

7. The solution composition encapsulating body according to claim 1, wherein a concentration of the chlorite is 500-50,000 ppm.

8. The solution composition encapsulating body according to claim 1, wherein the chlorite is sodium chlorite, and a concentration of the sodium chlorite is 700-20,000 ppm.

9. The method according to claim 1, wherein the chlorite is sodium chlorite, and a concentration of the sodium chlorite is 700-20,000 ppm.

10. The method according to claim 3, wherein the chlorite is sodium chlorite, and a concentration of the sodium chlorite is 700-20,000 ppm.

\* \* \* \* \*